United States Patent
McClure et al.

(10) Patent No.: US 6,711,438 B1
(45) Date of Patent: Mar. 23, 2004

(54) METHOD AND APPARATUS FOR BLANKING T-WAVES FROM COMBIPOLAR ATRIAL CARDIAC SIGNALS BASED ON EXPECTED T-WAVE LOCATIONS

(75) Inventors: Kelly H. McClure, Simi Valley, CA (US); Joseph J. Florio, La Canada, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 232 days.

(21) Appl. No.: 10/033,410

(22) Filed: Oct. 25, 2001

(51) Int. Cl.[7] ............................................. A61N 1/362
(52) U.S. Cl. ........................................................ 607/9
(58) Field of Search ......................................... 607/4–26

(56) References Cited

U.S. PATENT DOCUMENTS

| | | | |
|---|---|---|---|
| 5,466,254 A | 11/1995 | Helland ..................... 607/123 |
| 5,522,855 A | 6/1996 | Hoegnelid ..................... 607/9 |
| 6,539,259 B1 * | 3/2003 | Weinberg et al. | |

* cited by examiner

*Primary Examiner*—Scott M. Getzow (57) ABSTRACT

The stimulation device blanks T-waves from the atrial channel of an electrical cardiac signal by employing a T-wave blanking interval localized to the expected location and duration of the T-wave. To this end, the stimulation device determines the average interval between an R-wave and a T-wave in the patient in which the device is implanted and also determines the average duration of a T-wave within the patient. A T-wave blanking interval is initiated following the average R-T interval subsequent to detection of an R-wave and lasts for a period of time equal to the average T-wave duration. In this manner, highly localized T-wave blanking is achieved permitting P-waves or other atrial signals to be detected during remaining non-blanked portions of the atrial channel of the cardiac signal at least for the purposes of atrial rate detection. The relatively short T-wave blanking interval of the invention is particularly well suited for use in combipolar sensing systems. Method and apparatus implementations are described.

13 Claims, 6 Drawing Sheets

METHOD AND APPARATUS FOR BLANKING T-WAVES FROM COMBIPOLAR ATRIAL CARDIAC SIGNALS BASED ON EXPECTED T-WAVE LOCATIONS

CROSS-REFERENCE TO RELATED APPLICATIONS

This application is related to commonly-assigned U.S. patent application Ser. No. 09/354,244, filed Oct. 25, 2001, titled METHOD AND APPARATUS FOR BLANKING T-WAVES FROM COMBIPOLAR ATRIAL CARDIAC SIGNALS BASED ON EXPECTED T-WAVE LOCATIONS, now issued as U.S. Pat. No. 6,539,259.

FIELD OF THE INVENTION

The invention generally relates to implantable cardiac stimulation devices, such as pacemakers or implantable cardioverter-defibrillators ("ICDs") and, in particular, to techniques for processing electrical cardiac signals detected using combipolar sensing.

BACKGROUND OF THE INVENTION

A pacemaker is a medical device, typically implanted within a patient, which recognizes various dysrhythmias such as an abnormally slow heart rate (bradycardia) or an abnormally fast heart rate (tachycardia) and delivers electrical pacing pulses to the heart in an effort to remedy the dysrhythmias. An ICD is a device, also implantable into a patient, which additionally recognizes atrial fibrillation (AF) or ventricular fibrillation (VF) and delivers electrical shocks to terminate fibrillation.

Pacemakers and ICD's carefully monitor characteristics of the heart such as the heart rate to detect dysrhythmias, discriminate among different types of dysrhythmias, identify appropriate therapy, and determine when to administer the therapy. The heart rate is tracked by the device by examining electrical signals that are manifest concurrent with the contraction and expansion of the chambers of the heart. The contraction of atrial muscle tissue is manifest by the generation of a P-wave. The contraction of ventricular muscle tissue is manifest by the generation of an R-wave (sometimes referred to as the "QRS complex"). Expansion of the ventricular tissue is manifest as a T-wave. Expansion of the atrial tissue usually does not result in a detectable signal. The sequence of electrical events that represent P-waves, followed by R-waves (or QRS complexes), followed by T-waves are sensed using sensing leads implanted inside the heart, e.g., sensing leads.

One commonly used type of sensing lead is the unipolar lead, which includes a single electrode at its tip. The device detects electrical voltage differentials between the electrode and the external body of the device itself. Typically, one unipolar lead is inserted within the atria and another within the ventricles, from which the device derives separate atrial and ventricular channel cardiac signals. Another commonly employed type of sensing lead is the bipolar lead wherein the lead includes two electrodes mounted near its tip. The device detects electrical voltage differentials between the two electrodes. Again, typically, one lead is inserted within the atria and another within the ventricles, from which the device derives separate atrial and ventricular channels of cardiac signals.

A common problem with unipolar leads is that, because the device is sensing voltage differentials between the tip of the lead and the body of the device, significant far-field electrical signals are detected along with the intended atrial or ventricular cardiac signals. A "far-field" signal is a signal originating far from the sensor of the sensing lead, but detected by the sensing lead nonetheless. For example, the atrial cardiac signal derived from the atrial lead will typically include significant ventricular signals. A significant advantage of the bipolar lead is that, because electrical voltage differentials are detected only between two electrodes located closely adjacent to one another at the end of the lead, far-field sensing is significantly reduced. However, bipolar leads are more expensive and are generally perceived as being less reliable than unipolar leads and hence are not preferred by all physicians.

In an attempt to provide the advantages of bipolar sensing using unipolar leads, some state-of-the-art devices employ combipolar sensing techniques. With combipolar sensing, a pair of unipolar leads are mounted within the heart, one in the atria and one in the ventricles. A ventricular channel cardiac signal is generated in the same manner as with conventional unipolar sensing wherein electrical voltage differentials are detected between the tip of the ventricular lead and the body of the device. However, the atrial channel of the cardiac signal is generated by detecting voltage differentials between the electrodes at the tips of the atrial and ventricular leads. For a more complete description of combipolar systems, see U.S. Pat. No. 5,522,855 (Hognelid), incorporated herein by reference.

With combipolar sensing, because the atrial channel is derived based upon voltage differentials between the tips of the two unipolar leads, improved detection of atrial signals is achieved as compared with systems which require the relatively weak atrial electrical signals to be detected based upon voltage differentials generated between the tip of the atrial lead and the body of the device. Ventricular electrical signals are typically much greater in magnitude than atrial signals, hence, with the combipolar sensing technique, it is sufficient to sense the ventricular signals based upon voltage differentials generated between the tip of the ventricular lead and the body of the device. Hence, an overall improvement in the sensitivity of the detection of atrial signals is achieved using combipolar sensing, yet the perceived benefits of unipolar leads are retained, namely that the leads are less expensive and more reliable.

Thus, combipolar sensing provides many advantages. One disadvantage, however, is that, because the atrial channel is detected based upon voltage differentials between the tips of the atrial and ventricular leads, ventricular signals are sensed as "near-field" signals. As a result, ventricular signals may have a greater magnitude on the atrial channel than the atrial signals. Hence it may be difficult to filter the ventricular signals from the atrial channel. (The ventricular channel, because it is detected based upon voltage differentials between the tip of the ventricular lead and the body of the device, may also pick up far-field atrial signals, but these are typically very weak as compared to the ventricular signals and hence can easily be filtered out.)

Regardless of the electrode configuration being used, there is a need for the implanted device to be able to readily and reliably distinguish between various electrical events such as P-waves, R-waves and T-waves. For example, it is of critical importance that the device be capable of recognizing the occurrence of certain atrial arrhythmias based on the sensed atrial rate, and in determining such rate it is critically important that neither R-waves nor T-waves be falsely sensed as a P-wave. Such may be particularly problematic when an combipolar electrode configuration is being used because, as noted, P-waves, R-waves, and T-waves may be sensed as being of the same order of magnitude on the atrial channel. This problem exacerbated during an automatic mode switch (AMS), e.g., when switching the device from a DDD mode to a VVI or DDI mode. DDD, VVI and DDI are standard device codes which identify the mode of operation of the device. DDD indicates a device which senses and paces in both the atria and the ventricles and is capable of both triggering and inhibiting functions based upon sensed events. VVI indicates that the device is capable of pacing and sensing only within the ventricle and is only capable of inhibiting the functions based upon sensed events. DDI is identical to DDD except that the device is only capable of inhibiting functions based upon sensed events, rather than triggering functions. Numerous other device modes of operation are possible, each represented by standard abbreviations of this type.

One technique commonly employed for processing the atrial or ventricular channel signals to eliminate unwanted signals uses "blanking intervals". With a blanking interval, the device does not process electrical signals during a predetermined interval of time either for all device functions (absolute blanking) or for selected device functions (relative blanking). As one example of absolute blanking, upon detection of an R-wave on the ventricular channel, the device will not detect any signals on the atrial channel during a post ventricular atrial blanking (PVAB) interval. The atrial blanking interval is provided to prevent the device from erroneously responding to a far-field R-wave on the atrial channel. As one example of relative blanking, upon detection of an R-wave on the ventricular channel, the device will ignore all signals detected on the atrial channel during a post-ventricular atrial refractory period (PVARP) as far as the triggering or inhibiting of pacing functions is concerned, but not for other functions such as detecting and recording diagnostic information, particularly detection of premature atrial contractions (PACs). Pacemakers and ICDs may employ both the PVAB and the PVARP, with the PVAB being much shorter than the PVARP interval.

Figure 1:
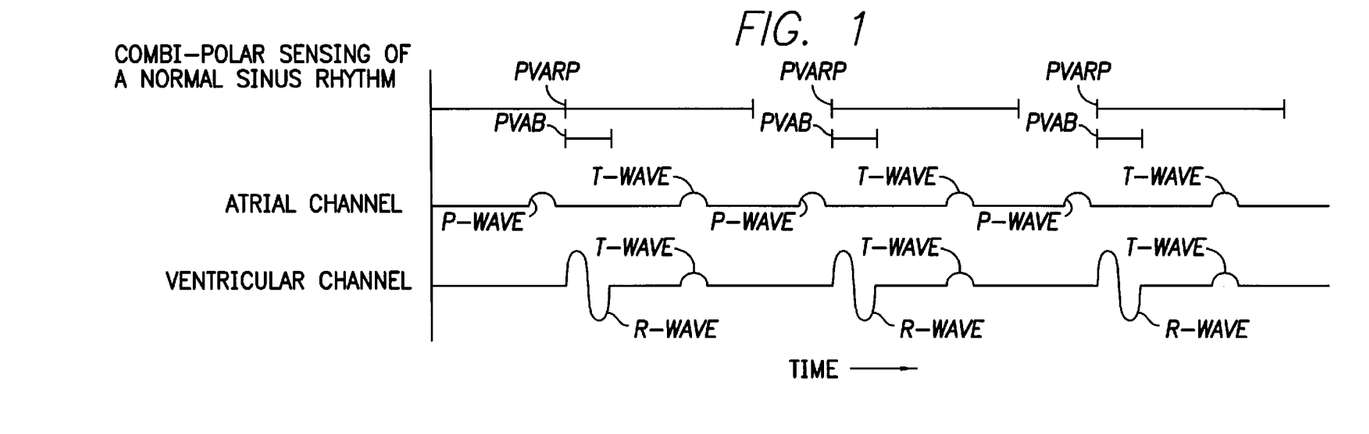
FIG. 1 is a graph illustrating exemplary atrial and ventricular channels of cardiac signals detected using combipolar sensing during normal sinus rhythm.

The effect PVAB and PVARP intervals is illustrated in FIG. 1 which shows a stylized representation of one atrial and one ventricular cardiac channel of a normal sinus rhythm detected using combipolar sensing. (Actual devices typically employ multiple atrial and ventricular channels to track different types of information. For example, one atrial channel may be employed for bradycardia detection, whereas another is employed for controlling AMS operations. For clarity in describing the effect of the PVAB and PVARP intervals, FIG. 1 illustrates only a single atrial channel and a single ventricular channel). The ventricular channel includes R-waves and T-waves. The atrial channel includes P-waves as well as ventricular T-waves, detected as near-field waves. FIG. 1 also illustrates the PVAB and PVARP intervals applied to the atrial channel. The PVAB interval, which begins upon detection of an R-wave on the ventricular channel, is set to a duration sufficient to cover the R-wave such that the R-wave is not detected in the atrial channel. The PVARP blanking interval is set to a length such that the T-wave, although detected on the atrial channel, is ignored. Hence, within the atrial channel, for the purposes of atrial rate detection, only events detected outside of the PVARP interval are used for the rate calculation. With proper setting of the PVARP and PVAB intervals, only P-waves are typically detected, and hence an accurate calculation of the true atrial rate is achieved for normal sinus rhythm.

Hence, blanking schemes may be used to blank T-waves from the atrial channel to prevent such T-waves from being falsely sensed as P-waves. However, such blanking schemes have proven less than satisfactory because P-waves may occur during the blanking intervals. Hence, the device may significantly underestimate the true atrial rate, and thereby fail to detect the tachyarrhythmia, flutter or fibrillation occurring in the atria. Thus, improper therapy may be administered.

Figure 2:
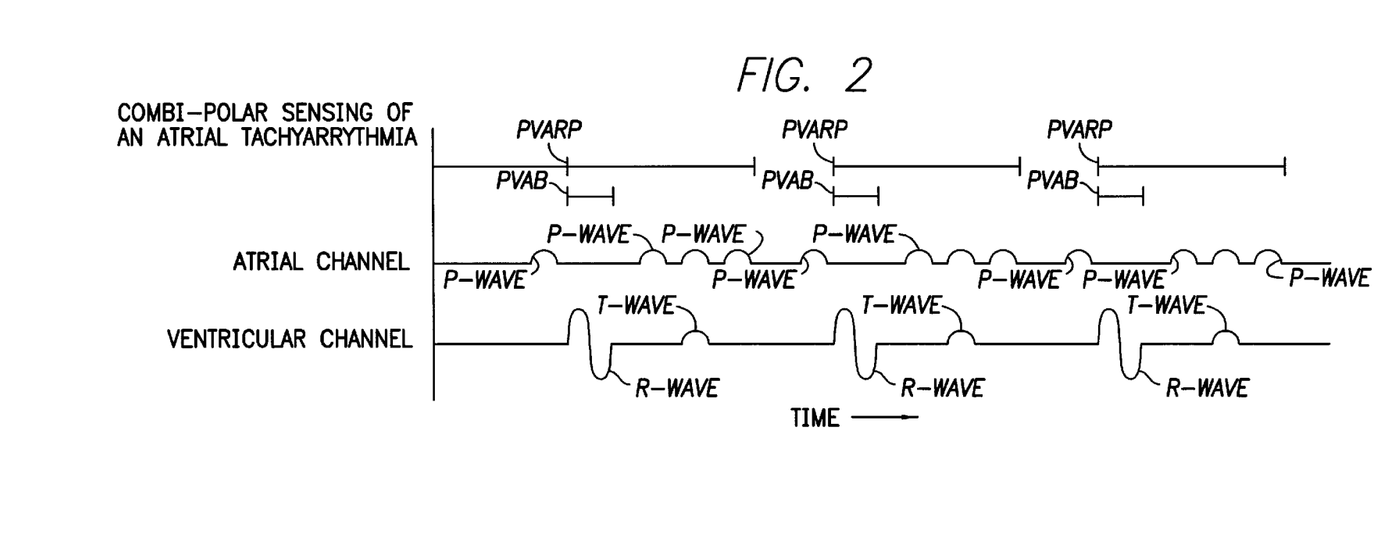
FIG. 2 is a graph illustrating exemplary atrial and ventricular channels of cardiac signals detected using combipolar sensing during an episode of atrial tachyarrhythmia.

FIG. 2 illustrates stylized atrial and ventricular channel cardiac signals detected using combipolar sensing during an episode of atrial tachyarrhythmia. As can be seen from the atrial cardiac signal, the frequency of P-waves is far greater than in FIG. 1. As a result, at least two P-waves occur during the PVARP interval, which are therefore ignored for the purposes of atrial rate detection. As a result, the atrial rate is substantially underestimated, possibly resulting in failure of the implantable device to administer appropriate anti-tachycardia pacing. FIG. 2 illustrates an extreme situation wherein a significant underestimation of the atrial rate can occur. But even in more benign circumstances, occasional P-waves may be blanked by the PVARP interval resulting in a slight underestimation of the atrial rate, perhaps sufficient to trigger an unnecessary mode switching or the like.

One solution that has been proposed for providing a better estimate of the atrial rate is to include events detected during the PVARP for the purposes of atrial rate calculations. Using this technique, P-waves detected during the PVARP are thereby sensed. However, T-waves may also be sensed during the PVARP interval resulting in an overestimation of the atrial rate, perhaps sufficient to trigger unnecessary anti-tachyarrhythmia therapy or at least sufficient to trigger an unnecessary mode switch.

Hence, there is a significant need to provide an improved technique for determining the true atrial rate. This need is particularly significant when using combipolar sensing, but also arises when using other electrode configurations such as conventional unipolar or bipolar sensing where T-waves may be detected on an atrial channel as far-field events.

SUMMARY OF THE INVENTION

In accordance with the invention, a method is provided for generating a T-wave blanking interval using an implantable cardiac stimulation device. In accordance with the method, the stimulation device senses a cardiac signal, identifies expected locations and durations of T-waves within the cardiac signal, and then blanks a portion of an atrial channel of the cardiac signal to ignore signals occurring within a period of time corresponding to the expected locations and durations of the T-waves. By localizing the T-wave in this manner, then blanking it from the atrial channel from which the atrial rate is derived, a more correct determination of the true atrial rate can be obtained.

Within an exemplary embodiment, the cardiac signal processed by the stimulation device includes electrical signals output from sense amplifiers of the stimulation device or includes intracardiac electrogram (IEGM) signals. The step of identifying the expected locations and durations of T-waves within the cardiac signal includes the steps of identifying an R-wave in the cardiac signal, tracking a first predetermined interval of time subsequent to the R-wave, which is representative of the expected interval between an R-wave and the beginning of a successive T-wave, and tracking a second predetermined interval of time subsequent to the beginning of the T-wave, which is representative of the expected duration of the T-wave. The expected interval between the R-wave and the T-wave (i.e., the R-T interval) and the expected duration of the T-wave are determined in advance by measuring and averaging R-T intervals and T-wave durations for a set of R-wave/T-wave pairs. Preferably, statistical information representative of a large number of R-wave/T-wave pairs is maintained, including information pertaining to the minimum and maximum voltages of the R-waves and T-waves, the durations of the R-waves and T-waves, and the intervals between the R-waves and T-waves. Also, preferably, the statistical information includes averages and standard deviations for these values. Periodically, to accommodate possible changes in the R-T interval and T-wave duration, additional R-wave/T-wave pairs are analyzed and the statistical information is adjusted accordingly. Also, preferably, before actually modifying the statistical information, a determination is made as to whether the characteristics of the newly detected R-wave/T-wave pairs deviate from the recorded average by no more than a predetermined amount, such as by no more than the first standard deviation. In this manner, the statistical information, from which the expected locations and durations of the T-waves are determined, is not improperly adjusted based upon anomalous R-wave/T-wave pairs, perhaps detected during flutter or fibrillation.

Apparatus embodiments of the invention are also provided. Other objects, features and advantages of the invention will be apparent from the detailed descriptions, which follow in combination with the accompanying drawings.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE INVENTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 3:
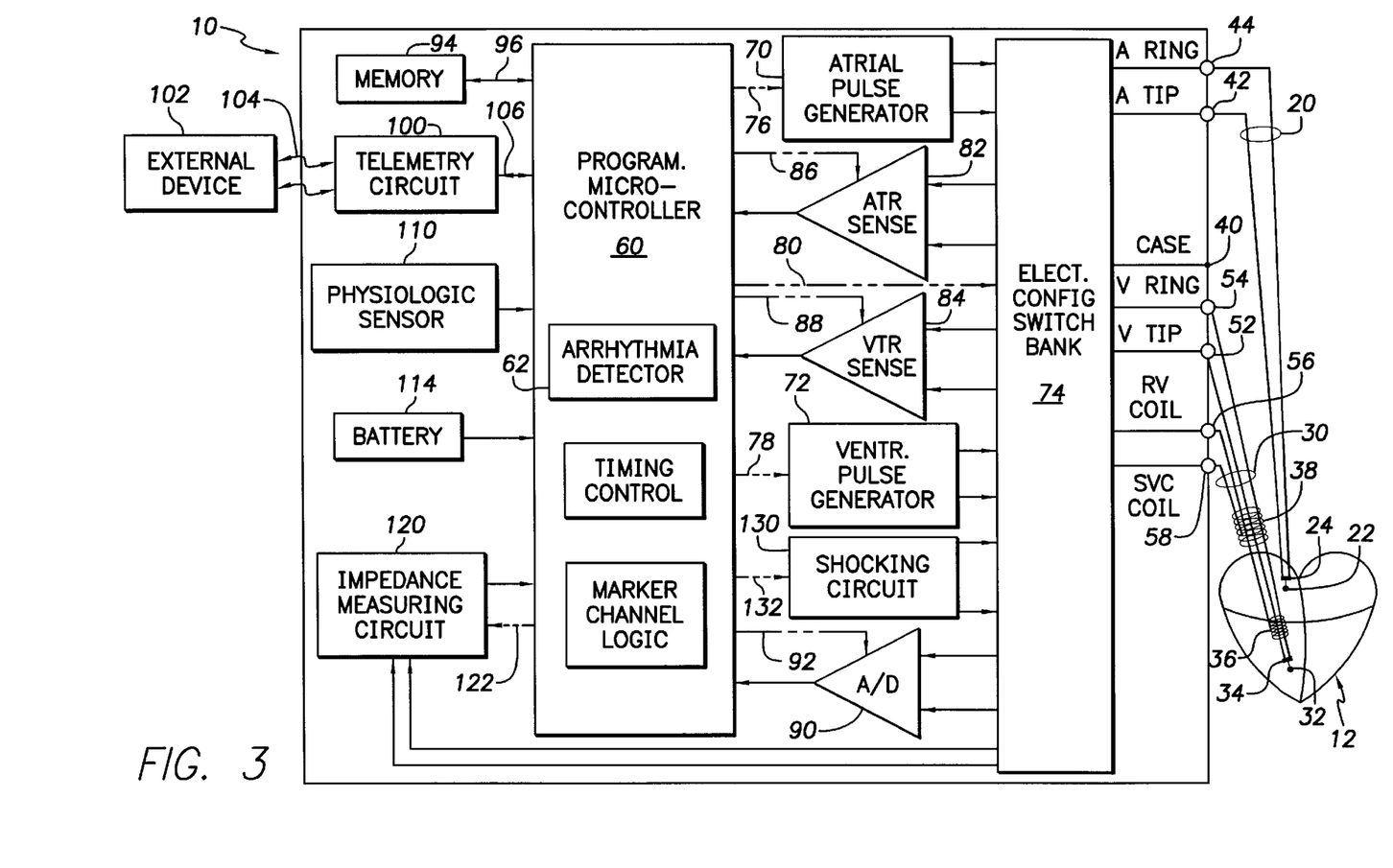
FIG. 3 is a functional block diagram of a dual-chamber implantable stimulation device illustrating the basic elements of a stimulation device which can provide cardioversion, defibrillation and pacing stimulation.

In FIG. 3, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an superior vena cava (SVC) coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 3, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of a coronary sinus lead, see U.S. patent application Ser. No. 09/457,277, "A Self-Anchoring, Steerable Coronary Sinus Lead" (Pianca et al.), and U.S. Pat. No. 5,466,254, "Coronary Sinus Lead with Atrial Sensing Capability" (Helland), which patents are hereby incorporated herein by reference.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

At the core of the stimulation device 10 is a programmable microcontroller 60 which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art. As shown in FIG. 3, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses, that is known in the art. The controller also includes a T-wave blanking system described in greater detail below.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art. An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation. The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers.

For arrhythmia detection, the invention utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., P-P, R-R and R-T intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire cardiac signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 28 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70 and 72, generate stimulation pulses. The type of sensor used is not critical to the invention and is shown only for completeness. The stimulation device additionally includes a battery 114 which provides operating power to all of the circuits shown in FIG. 3. For the stimulation device 10, which employs shocking therapy, the battery must be capable of operating at low current drains for long periods of time (preferably less than 10_A), and then be capable of providing high-current pulses (for capacitor charging) when the patient requires a shock pulse (preferably, in excess of 2 A, at voltages above 2 V, for periods of 10 seconds or more). The battery 114 must also have a predictable discharge characteristic so that elective replacement time can be detected. Accordingly, the invention employs lithium/silver vanadium oxide batteries, as is true for most (if not all) such devices to date. As further shown in FIG. 3, the invention preferably includes an impedance measuring circuit 120 which is enabled by the microcontroller 60 by a control signal 122. The impedance measuring circuit 120 is not critical to the invention and is shown for only completeness.

Depending upon the implementation, the device may function as an implantable cardioverter/defibrillator (ICD) device. That is, it detects the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 4:
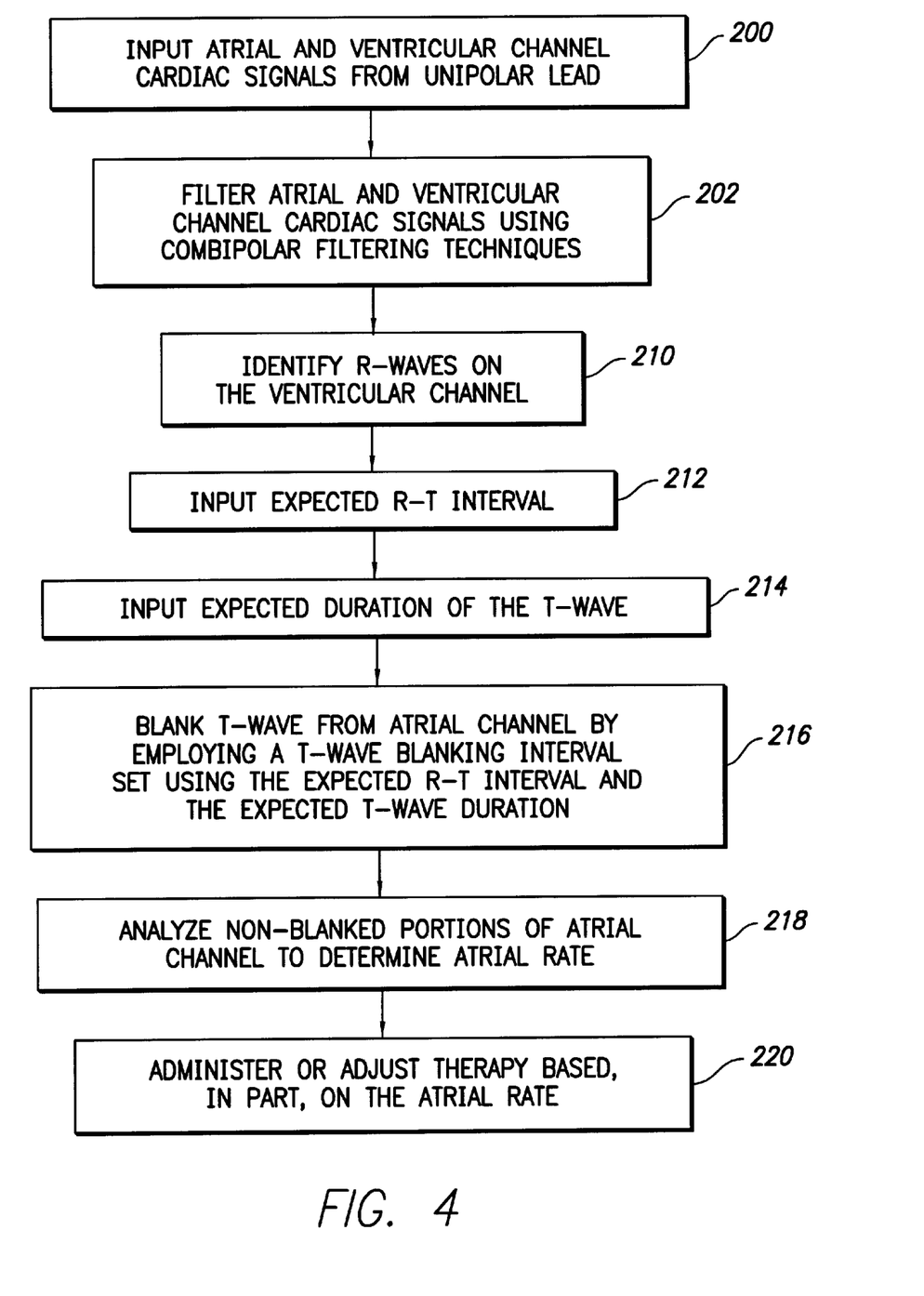
FIG. 4 is a flow chart illustrating a method performed by the system of FIG. 3 for blanking T-waves from an atrial channel cardiac signal based upon predetermined information identifying the location and duration of the T-wave relative to a preceding R-wave.

FIG. 4 is a flow chart illustrating the operation of the T-wave blanking method of the invention. In the flow chart, the various steps of the method are summarized in individual "blocks". Such blocks describe specific actions or decisions that are made or carried out as the method proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Within FIG. 4, at step 200, the implantable cardiac stimulation device inputs atrial and ventricular channel cardiac signals from a pair of unipolar leads, one positioned within the atria, the other within the ventricles. In the following, for the purposes of describing the concepts of the T-wave blanking method of the invention, only a single atrial channel and a single ventricular channel will be described. The atrial channel is a channel from which the atrial rate is detected. In some cases this may be also employed as an automatic mode switch channel or perhaps a bradycardia detection channel. In practical systems, numerous atrial and ventricular channels may be employed, each used for different purposes. In any case, the atrial channel cardiac signal represents a voltage differential between the tip of the atrial lead and the tip of the ventricular lead. The ventricular channel cardiac signal represents a voltage differential between the tip of the ventricular lead and the body of the implantable medical device. The device, at step 202, filters the atrial and ventricular channels using combipolar filtering techniques to eliminate noise and the like and to enhance the true atrial components of the atrial channel. Combipolar filtering techniques are well known in the art and will not be described in detail herein. Further information may be found in the above-referenced patent to Hognelid.

To eliminate the R-waves and T-waves from the atrial channel, the implantable device, at step 210 of FIG. 4, identifies R-waves on the corresponding ventricular channel (not shown) and blanks any events detected simultaneously on the atrial channel. Identification of R-waves may be performed using any conventional R-wave detection technique. In the event the medical device is currently pacing the ventricles, then the device merely ignores any events detected on the atrial channel simultaneous with administration of pacing pulses to the heart. In this manner, R-waves or ventricular paced events are blanked from the atrial channel so as not to interfere with the correct determination of the atrial rate. Also, by identifying R-waves on the ventricular channel, the device can then begin to determine the expected location of the T-wave relative to the R-wave for blanking the atrial channel during the T-wave. To this end, the device, at step 212, inputs from stored memory the expected R-T interval, i.e., the time interval between the R-wave and the expected T-wave. Preferably, the R-T interval represents the expected amount of time between the end of the R-wave and the beginning of the T-wave. However, in other implementations, the R-T interval may instead represent the expected interval of time between the mid-point of the R-wave and the mid-point of the T-wave, or between any other pair of identifiable points within the R- and P-waves. At step 214, the device then inputs the expected duration of the T-waves from recorded memory.

Figure 5:
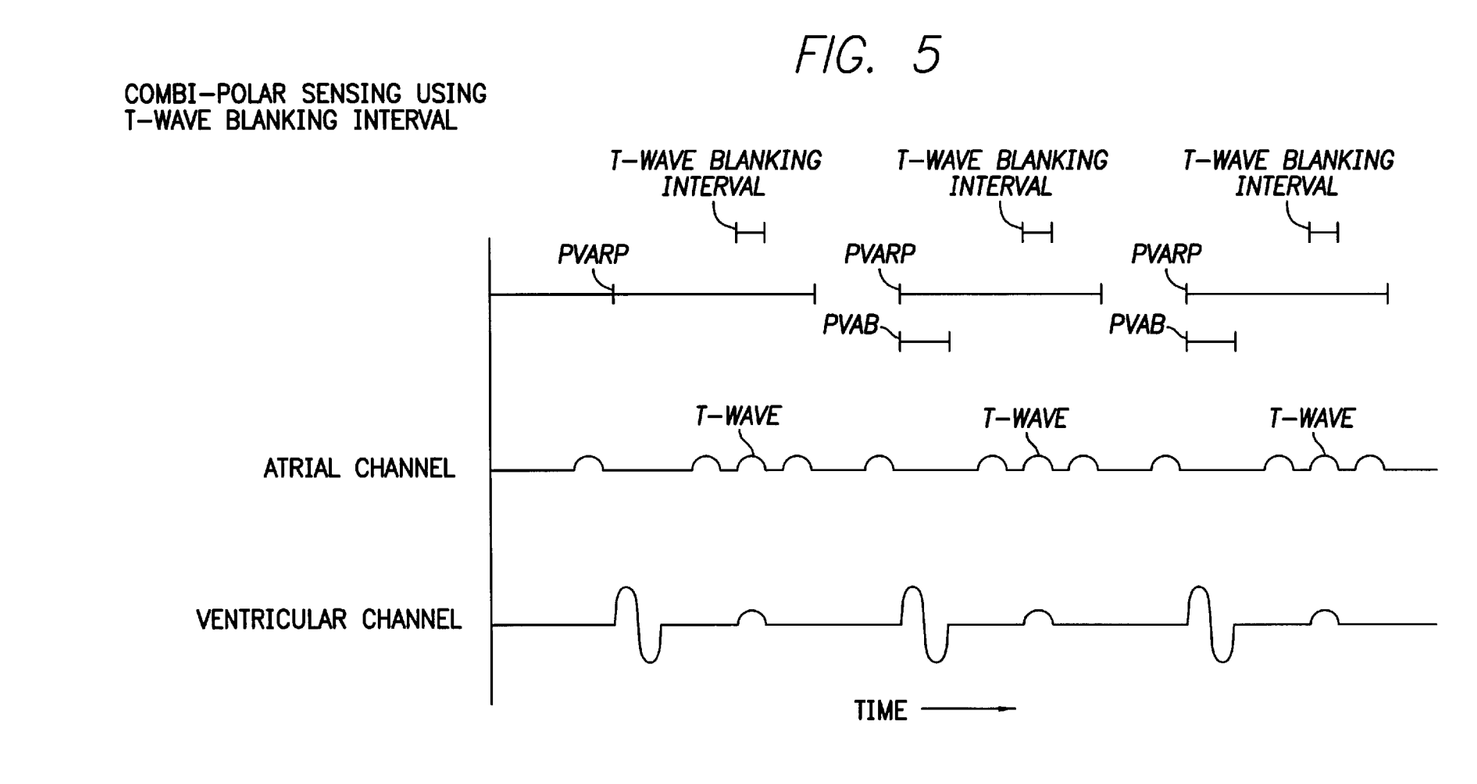
FIG. 5 is a graph illustrating exemplary atrial and ventricular channels of cardiac signals detected during a period of atrial tachyarrhythmia using combipolar sensing and specifically illustrating a T-wave blanking interval set to the expected location of T-waves within the cardiac signals.

The device then blanks a portion of the atrial channel, at step 216, using a T-wave blanking interval set using the expected R-T interval and the expected T-wave duration. More specifically, the device utilizes a timer to track the expected R-T interval beginning at the end of the R-wave. Once the timer has elapsed, the device then ignores electrical signals detected on the atrial channel, at least for the purposes of atrial rate detection. When the blanking interval begins, the device activates a second timer which times the expected duration of the T-wave as retrieved from recorded memory. Once the second timer has elapsed, the device then resumes detecting and processing signals on the atrial channel at least for the purposes of atrial rate detection. The T-wave blanking interval is illustrated in FIG. 5 as interval 217.

At step 218, the device then analyzes the non-blanked portions of the atrial channel to determine the atrial rate. The atrial rate is determined, pursuant to conventional techniques, by tracking P-waves detected within non-blanked portions of the atrial channel. P-waves may be detected, for example, by identifying all electrical events having a magnitude exceeding a predetermined threshold representative of the magnitude of P-waves. Since the R-waves are blanked at step 210 and the T-waves are blanked at step 216, any events exceeding the predetermined P-wave threshold on the atrial channel most likely represent true P-waves originating in the atria. The device counts the number of P-waves during a predetermined period of time and determines therefrom the atrial rate.

At step 220, the device then administers or adjusts stimulation therapy based, in part, on the detected atrial rate. Within step 220, any conventional pacemaker or ICD function affected by the detection of discrete P-waves, the detection of the atrial rate, or the detection of any other events on the atrial channel may be performed. By way of example, the device may administer anti-bradycardia pacing, anti-tachycardia pacing or other forms of pacing therapy or may administer cardioversion pulses to terminate fibrillation in the atria or ventricles.

Within a state-of-the-art pacemaker or ICD, numerous functions performed by the device may be affected by the determination of the atrial rate or by other characteristics identified from the atrial channel of the cardiac signal. In some cases, the administration of therapy or performance of other functions are triggered by detection of such events. In other cases, the administration of therapy or the performance of other functions is inhibited by the detection of such events. No attempt is made herein to identify the many functions which may be affected by events detected on the atrial channel.

By eliminating only R-waves and T-waves from the atrial channel, the detection of true atrial events and the true atrial rate is thereby improved, which benefits the many functions affected by detection of atrial events. This is in contrast with many conventional atrial channel blanking techniques, illustrated in FIGS. 1 and 2, wherein either all events detected during a PVARP interval are ignored for the purposes of atrial rate detection or wherein all events, including T-waves detected during the PVARP, are used for the purposes of atrial rate detection. By eliminating all events during the PVARP interval, a significant underestimation of the true atrial rate may occur. By using all events detected during the PVARP an overestimation of the true atrial rate may occur.

Figure 6:
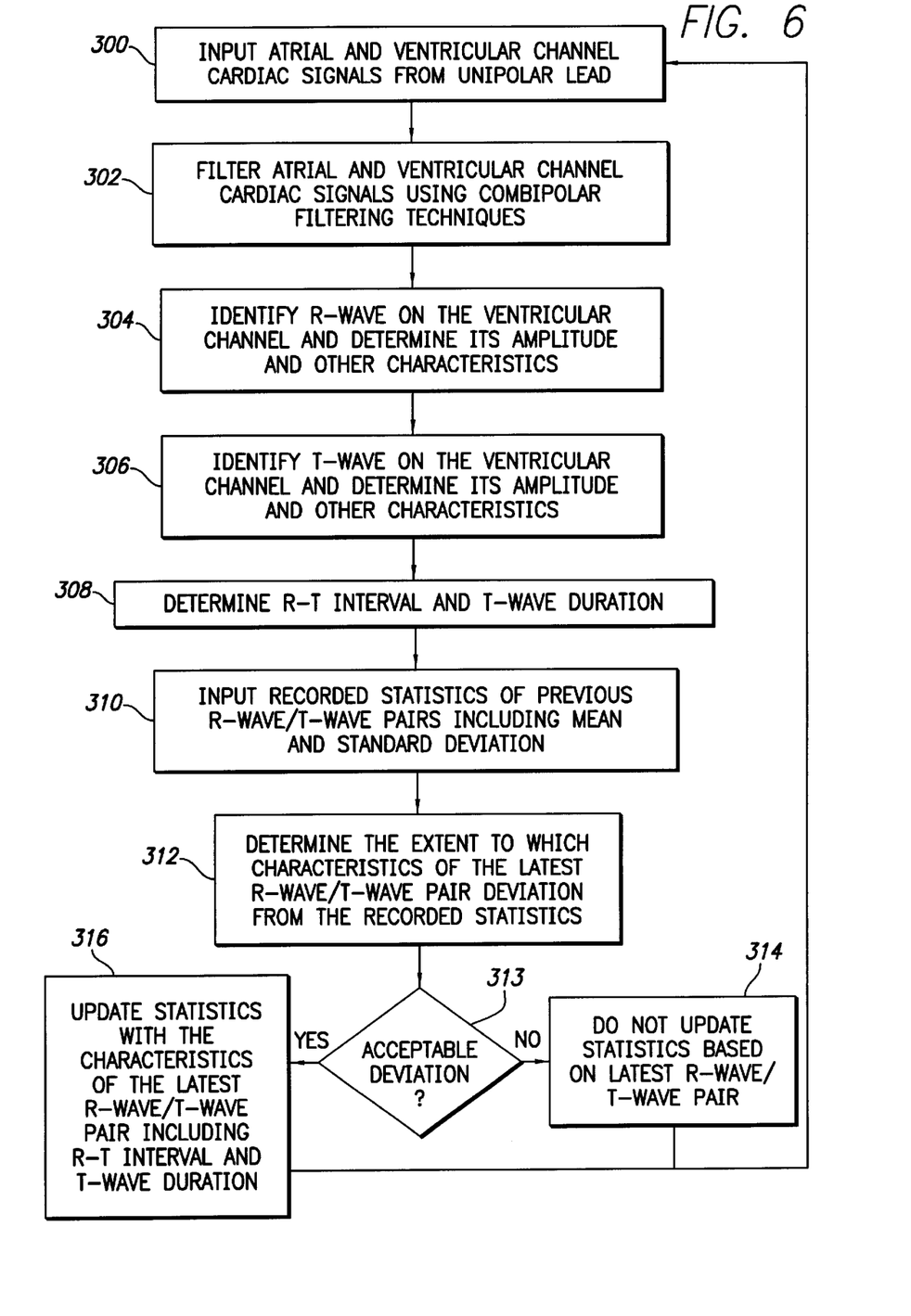
FIG. 6 is a flow chart illustrating a method performed by the system of FIG. 3 for determining the expected location and duration of T-waves relative to R-waves for use by the method of FIG. 4.

Thus, what has been described with reference to FIG. 4, is a method which utilizes a predetermined expected R-T interval and a predetermined expected T-wave duration to localize the expected position of T-waves on the atrial channel for blanking thereof. With reference to FIG. 6, a method for determining and updating the expected R-T interval and the expected T-wave duration is illustrated. Briefly, the method of FIG. 6 is periodically performed by the device to determine the average R-T interval and average T-wave duration for the patient in which the device is implanted. The device stores these averages in memory for use during processing of the method of FIG. 4. The method of FIG. 6 may be performed, for example, once per hour, once per day, or at any other programmed frequency, as programmed by the physician. Alternatively, the method of FIG. 6 may be performed on demand, perhaps if the device begins to detect anomalous behavior indicative of erroneous detection of T-waves as being P-waves or it may be performed in response to the onset of exercise or a change in posture or based or a significant change in heart rate. The method of FIG. 6 operate continuously updating information as often as every cardiac cycle and thus providing a near continuous estimate of the information acquired using the method of FIG. 6.

In any case, at step 300, the device inputs atrial and ventricular channel cardiac signals from unipolar leads and, at step 302, processes the channels using combipolar filtering techniques to yield atrial and ventricular channels having discrete and identifiable P-waves, R-waves, and T-waves. At step 304, the device identifies an R-wave on the ventricular channel and determines its amplitude and other characteristics. Depending upon the specific programming of the system, the device may, for example, identify the maximum voltage, the minimum voltage and the duration of the R-wave, along with the maximum and minimum slopes of the R-wave (i.e., the maximum and minimum first derivatives of the instantaneous amplitude of the ventricular channel cardiac signal during the R-wave). At step 306, the device identifies the immediately succeeding T-wave on the ventricular channel and determines its amplitude and other characteristics.

Identification of a T-wave at step 306 may be determined, in accordance with the invention, by identifying a relatively flat period of the ventricular cardiac signal subsequent to the end of the R-wave, then detecting an increase in the amplitude of the cardiac signal above a predetermined T-wave amplitude threshold. Alternative techniques may be employed to compare portions of the ventricular channel cardiac signal with predetermined templates representative of T-waves until a suitable match is achieved. Note that the analysis is performed with respect to the ventricular channel in which far-field atrial signals are likely to be extremely low in amplitude. Hence, there is little or no risk that a P-wave detected on the ventricular channel will be misidentified as a T-wave. Depending upon the amount of noise in the system, however, there is some risk that a noise artifact or some other anomalous electrical signal, perhaps originating elsewhere in the body, may be initially misidentified as being a T-wave. Accordingly, steps, to be described below, are provided to detect potentially erroneous T-waves so that they may be eliminated from further processing.

At step 308, the device then determines the interval of time between the R-wave and the T-wave and further determines the duration of the T-wave. As noted above, the R-T interval is preferably set to equal the duration of time between the end of the R-wave and the beginning of the T-wave but other specific intervals may alternatively be employed. Detection of the duration of the T-wave is performed, for example, by using a predetermined maximum noise threshold. Once the T-wave has been identified (perhaps based upon template matching or the like), the device then examines samples of the instantaneous voltage of the cardiac signal immediately before and after the maximum amplitude point of the T-wave to identify all samples exceeding the maximum noise threshold. The duration of the T-wave is then defined to be the time period between the point in time at which the ventricular cardiac signal rises above the maximum noise threshold to the point in time at which the ventricular signal again drops below the maximum noise threshold. Other techniques for defining and detecting the duration of the T-wave may alternatively be employed.

At step 310, the device then determines whether its internal memory already includes recorded statistics representative of the average R-T interval and the average T-wave duration. If so, the device a inputs the recorded statistics representative of previously processed R-wave/T-wave pairs, including the mean and standard deviations of the R-T interval and the T-wave duration. At step 312, the device then determines the extent to which the detected characteristics of the latest R-wave/T-wave pair deviate from the recorded statistics. If no statistics were retrieved at step 310, step 312 is simply skipped. If recorded statistics had been retrieved at step 310, and the characteristics of the latest R-wave/T-wave pair deviate significantly from the recorded statistics as determined at step 313, then, at step 314, the device ignores the latest R-wave/T-wave pair as being an anomalous pair. Otherwise, the device updates the recorded statistics, at step 316, using the characteristics of the latest R-wave/T-wave pair. For example, if at step 312, it is found that the R-T interval for the latest R-wave/T-wave pair is substantially greater than or less than the average R-T interval, then the device concludes that the latest pair of events represent an anomalous pair of events and the events are discarded. Likewise, if the duration of the latest T-wave is substantially greater than or less than the average duration of an average T-wave, then again the latest pair of events are discarded. Within step 312, other characteristics besides R-T interval and T-wave duration may be employed for the purposes of determining whether to update the prerecorded statistics. In general, any of the characteristics identified for the R-waves and T-waves may be employed for making this determination. For example, a significant variation between the average maximum slope of an R-wave and the maximum slope of the newly detected R-wave may be employed to eliminate the R-wave from further processing.

As can be appreciated, a wide range of characteristics or combinations of characteristics may be compared with the predetermined statistics for the purposes of discarding anomalous events. In making the determination of step 313, the device preferably takes into account the current ventricular rate of the patient. In general, the R-T interval decreases slightly with increasing ventricular rate. Accordingly, the R-T interval of the newly detected pair of ventricular events is preferably adjusted to compensate for any change in interval caused solely by ventricular rate prior to comparison with the prerecorded average R-T interval. In the alternative, different average R-T intervals may be recorded for different ranges of ventricular rates to permit the current R-T interval to be compared directly with the average R-T interval for the corresponding ventricular rate. As can be appreciated, numerous techniques may be employed for compensating for variations in the characteristics of the ventricular events as a function of ventricular rate, or other characteristics of the state of the ventricles.

If, during steps 310 and 312, the device determines that there are no prerecorded statistics for ventricular events, then the device begins to generate the statistics based upon the newly detected ventricular events. Once some minimum number of ventricular events have been processed sufficient to permit reliable statistics to be derived, such as six to twenty events, the device then permits the recorded statistics to be used for comparison against newly detected events at step 312. In this manner, the decision of step 313 is performed only if there is a sufficient amount of data recorded to ensure reliable operation. In the alternative, the device may be preprogrammed with statistics representative of the R-T interval, T-wave duration and other characteristics for typical patients. In this manner, the device of any particular patient need not generate statistics entirely based upon detected events but may begin by utilizing the preprogrammed statistics.

In any case, with continuous or periodic processing of the steps of FIG. 6, prerecorded statistics representative of the average R-T interval, T-wave duration and the like, are adjusted to take into account changes in these characteristics within the patient. Thus, if the patient takes any medications which may affect the R-T interval, the system will detect the change in the average R-T interval, and will update its recorded statistics accordingly, such that, during processing of the method of FIG. 4, the correct current expected R-T interval for the patient is employed. Likewise, the average T-wave duration is adjusted periodically or continuously within the device to permit the correct interval to be employed during the processing of the steps of FIG. 4. In general, the system thereby provides a feedback mechanism for ensuring that the expected R-T interval and expected T-wave duration are continuously readjusted to ensure correct blanking of T-waves from the atrial channel. Without this feedback mechanism, there is a risk that the blanking window employed within FIG. 4 would eventually deviate from the actual location of T-waves such that T-waves would begin to be detected outside the blanking interval and erroneously misidentified as P-waves. By providing the aforementioned feedback mechanism, there is little or no risk of this occurring and it is fairly certain that the T-wave blanking interval will almost always correspond with the actual location of T-waves on the atrial channel to permit reliable blanking thereof. Hence, the methods described herein provide an adaptive T-wave filter which adapts to the changes in the patient. Other adaptive filtering techniques may be employed to ensure that the R-T interval, the T-wave duration or any other characteristics used to localize the T-wave on the atrial channel.

Figure 7:
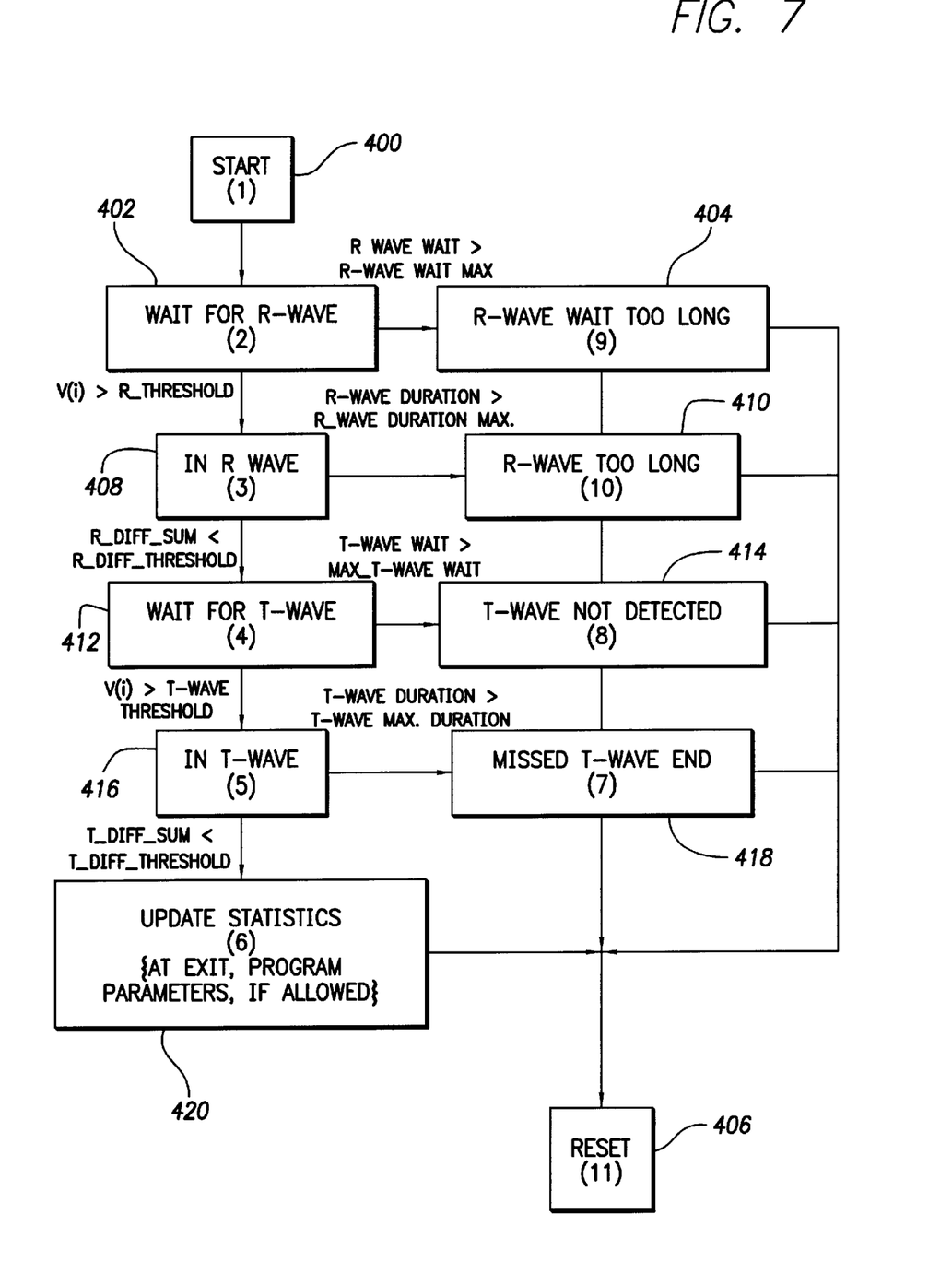
FIG. 7 is a flow chart illustrating a state machine employed by a controller of the system of FIG. 3 for detecting R-waves, then blanking T-waves in accordance with the general method illustrated in FIG. 2.

The methods described in FIGS. 4–6 may be implemented, for example, by programming the controller of FIG. 3 to operate as a state machine in accordance with the state machine diagram of FIG. 7. The state machine diagram of FIG. 7 generally corresponds with the methods already described and hence the state machine will only be summarized. Initially, the controller transitions from starting state 400 to state 402 wherein the controller performs operations directed to detecting an R-wave. If the controller remains in state 402 too long, e.g., the time in the R-WAVE WAIT state exceeds a threshold R-WAVE WAIT MAX, then it transitions through state 404 to reset state 406 and ultimately back to state 402. In this manner, R-waves detected after an inordinately long period of time are ignored for the purposes of T-wave blanking. While in the state 402, the device operates to detect the onset of an R-wave by checking for signal characteristics indicative of the onset of an R-wave, e.g., the absolute value of the R-wave, V(i), exceeds a limit R_THRESHOLD. If an R-wave is detected sufficiently promptly within state 402, the controller transitions to state 408 where it performs functions directed to detecting the various characteristics of the R-wave including, for example, its maximum and minimum voltages, duration, maximum and minimum slopes, and the like. If the duration of the R-wave detected during state 408 exceeds a predetermined threshold (e.g., R-WAVE DURATION>R_WAVE DURATION MAX), indicating that the R-wave is probably not a true R-wave but some other event, the controller transitions through state 410 to the reset state and ultimately back to state 402 for detection of another R-wave. Assuming that the duration of the R-wave detected during state 408 is not inordinately long, then the controller, upon completion of the R-wave, transitions to state 412 where the controller waits for detection of a T-wave. One approach to detecting completion of an R-wave during state 408 uses a non-linear filter operating on a digitally sampled R-wave signal. The R-wave is sampled at about 250 samples per second. Absolute values of differences between samples separated by 0.008 and 0.025 seconds are averaged over 0.01 to 0.04 seconds. These averaged differences, R_DIFF_SUM, seem to very effective at detecting the completion of an R-wave, e.g., R_DIFF_SUM<R_DIFF_THRESHOLD.

During state 412, the controller performs functions directed to detecting the next T-wave including, for example, monitoring the amplitude and slope of the ventricular cardiac signal until the amplitude and slope varies in accordance with the expected characteristics of the beginning of a T-wave (V(i)>T-WAVE THRESHOLD, where V(i) is, e.g., the amplitude or slope of the ventricular cardiac signal). If the controller remains in state 412 for too long (T-WAVE WAIT>MAX_T-WAVE WAIT), indicating a possibly anomalous event, the controller transitions through state 414 to reset state 406 and ultimately back to state 402 to detect another R-wave. If a T-wave is detected sufficiently promptly within state 412, the controller transitions to state 416 wherein the controller performs functions directed to processing the T-wave including, for example, detecting the amplitude and duration of the T-wave, as well as its maximum and minimum slopes and the like. If the duration of the T-wave detected within state 416 is too long, indicating that the event is a true T-wave, the controller transitions through state 418 to reset state 406 and ultimately back to state 402 for detection of yet another R-wave. If, however, the duration of the T-wave does not exceed the maximum expected duration and the completion of the T-wave is detected, the controller transitions to state 420. One approach to detecting completion of a T-wave during state 416 uses a non-linear filter operating on the a digitally sampled T-wave signal. The T-wave is sampled at about 250 samples per second. Absolute values of differences between samples separated by 0.008 and 0.032 seconds are averaged over 0.01 to 0.064 seconds. These averaged differences, T_DIFF_SUM, seem to very effective at detecting the completion of an R-wave, e.g., T_DIFF_SUM<T_DIFF_THRESHOLD.

While in state 420, the controller performs functions directed to generating statistics or updating statistics for R-wave/T-wave pairs. Once statistics have been generated or updated, the controller transitions to reset state 406, and ultimately to state 402 for detecting another R-wave.

Thus, FIG. 7 illustrates the various states of the controller for use in detecting R-wave/T-wave pairs and for updating the statistical representation thereof. This represents one example of the programming of the controller of the medical device. In the alternative, the controller may be programmed in accordance with other specific state machines or in accordance with other techniques to perform the general functions outlined above.

As can be appreciated, a wide variety of techniques are consistent with the general principles of the invention. The embodiments described herein are merely illustrative of aspects of the invention and should not be construed as limiting the scope of the invention which is to be interpreted in accordance with the claims that follow.

What is claimed is:

1. A method performed by an implantable cardiac stimulation device for blanking a portion of a cardiac signal, the method comprising:

sensing a cardiac signal;

identifying an expected location and duration of a T-wave within the cardiac signal; and blanking a portion of an atrial channel of the cardiac signal to ignore signals occurring within a period of time corresponding to the expected location and duration of the T-wave.

2. The method of claim 1 wherein the implantable cardiac stimulation device comprises unipolar leads adapted to be coupled to heart tissue and wherein sensing a cardiac signal comprises:

sensing atrial and ventricular channel cardiac signals using the unipolar leads; and filtering the atrial and ventricular channel cardiac signals using combipolar filtering.

3. The method of claim 1 further comprising:

analyzing non-blanked portions of the atrial channel of the cardiac signal to determine the behavior of the heart.

4. The method of claim 3 wherein analyzing the non-blanked portions of the atrial channel comprises detecting P-waves therein.

5. The method of claim 3 wherein analyzing the non-blanked portions of the atrial channel of the cardiac comprises detecting the atrial rate.

6. The method of claim 3 wherein analyzing the non-blanked portions of the atrial channel comprises detecting a dysrhythmia, if any, in the heart.

7. The method of claim 6 wherein the dysrhythmia is one of atrial flutter and atrial fibrillation.

8. The method of claim 3 further comprising:

controlling stimulation operations of the device based on the analysis of the non-blanked portions of the atrial channel of the cardiac signal.

9. The method of claim 8 wherein controlling stimulation operations comprises determining whether to trigger an auto-mode switching operation within the implantable cardiac pacing device.

10. The method of claim 1 wherein identifying the expected location and duration of a T-wave within the cardiac signal comprises:

identifying an R-wave in the cardiac signal;

tracking a first predetermined interval of time subsequent to the R-wave, the first predetermined time interval being representative of an expected interval between the end of an R-wave and the beginning of a successive T-wave; and tracking a second predetermined interval of time subsequent to the beginning of the T-wave, the second predetermined time interval being representative of an expected duration of a T-wave.

11. The method of claim 10 further comprising:

determining the first interval of time by measuring and averaging the intervals between a plurality of R-wave/T-wave pairs; and determining the second predetermined interval of time by measuring and averaging the durations of a plurality of T-waves.

12. A system for blanking a portion of a cardiac signal using an implantable cardiac stimulation device, the system comprising:

means for sensing a cardiac signal;

means for identifying an expected location and duration of a T-wave within the cardiac signal; and means for blanking portions of an atrial channel of the cardiac signal to ignore signals occurring within a period of time corresponding to the expected location and duration of the T-wave.

13. A system for blanking a portion of a cardiac signal using an implantable cardiac stimulation device, the system comprising:

a sensing system for sensing a cardiac signal; and a controller for identifying an expected location and duration of a T-wave within the cardiac signal and for blanking portions of an atrial channel of the cardiac signal to ignore signals occurring within a period of time corresponding to the expected location and duration of T-waves.

* * * * *